United States Patent [19]

Beddoe et al.

[11] Patent Number: 4,658,823
[45] Date of Patent: Apr. 21, 1987

[54] INCANDESCENT LAMP STRUCTURE FOR APPLYING THERAPEUTIC HEAT

[76] Inventors: Alexander F. Beddoe; Martha A. Beddoe, both of 32851 Mill Creek Dr., Fort Bragg, Calif. 95437

[21] Appl. No.: 852,433

[22] Filed: Apr. 15, 1986

[51] Int. Cl.[4] .................................................. A61F 7/00
[52] U.S. Cl. ....................................... 128/396; 128/399
[58] Field of Search .................. 128/395, 396, 399; 126/204

[56] References Cited

U.S. PATENT DOCUMENTS

| | | | |
|---|---|---|---|
| 881,017 | 3/1908 | Morse | 128/399 X |
| 1,771,076 | 7/1930 | Chesney | 128/396 |
| 1,953,206 | 4/1934 | Withrow | 128/395 |
| 2,120,872 | 6/1938 | Seward | 128/395 X |
| 2,232,156 | 2/1941 | Abeles | 128/395 |
| 3,089,033 | 5/1963 | Fujisawa | 128/399 X |
| 3,152,594 | 10/1964 | Kramer | 128/395 |
| 3,648,706 | 3/1972 | Holzer | 128/395 |
| 3,675,659 | 7/1972 | Wideman | 128/395 |
| 3,796,855 | 3/1974 | Brown et al. | 128/399 X |
| 3,867,948 | 2/1975 | Kallerborn | 128/395 |
| 4,381,009 | 4/1983 | Del Bon | 128/399 |
| 4,505,545 | 3/1985 | Salia-Munoz | 350/321 |

FOREIGN PATENT DOCUMENTS

| | | | |
|---|---|---|---|
| 454081 | 1/1949 | Canada | 128/396 |
| 1139096 | 2/1957 | France | 128/395 |

Primary Examiner—Anton O. Oechsle

[57] ABSTRACT

A therapeutic device to give the controlled application of heat to the live human ear and its structures thereof for the treatment of pain and congestion due to injury, inflammation, or infection. The lamp consists of an adjustable handle (10) attached to a mounting base (20) that holds a ceramic light bulb socket (36) which can hold approximately a 15 to 25 watt incandescent appliance light bulb as the heat source. The heat produced by the light bulb is controlled and directed to the point of application by a lamp housing (16) with an open end for placing over the ear. The lamp housing also has as a part of its structure an adjustable vent ring (24) with vent holes (26) and an upper limit sealed thermostat (32). The adjustable venting system along with the thermostat create a combination that allows for a simple, accurate, safe, and economical way of adding a new dimension for using light and heat in assisting in the treatment of earaches and ear infections, making it a mother's best friend. Also can be used in other applications where heat without undue pressure can be used to manage specific, but localized, inflammatory conditions.

2 Claims, 5 Drawing Figures

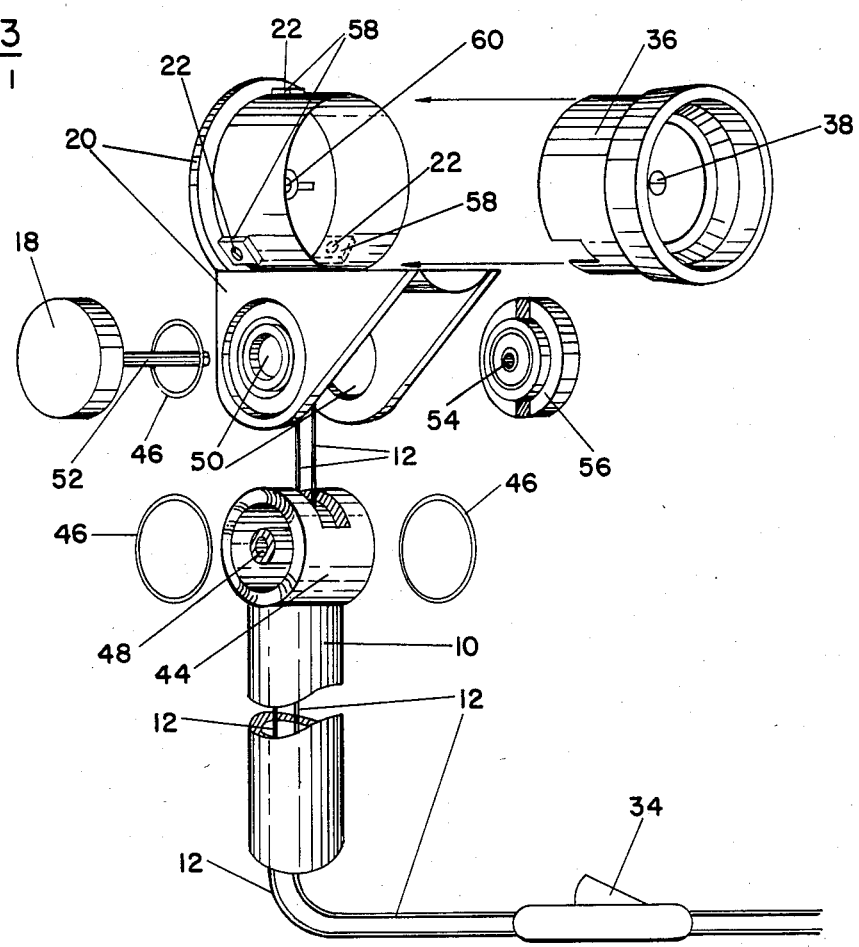
FIG. 3 PART 1
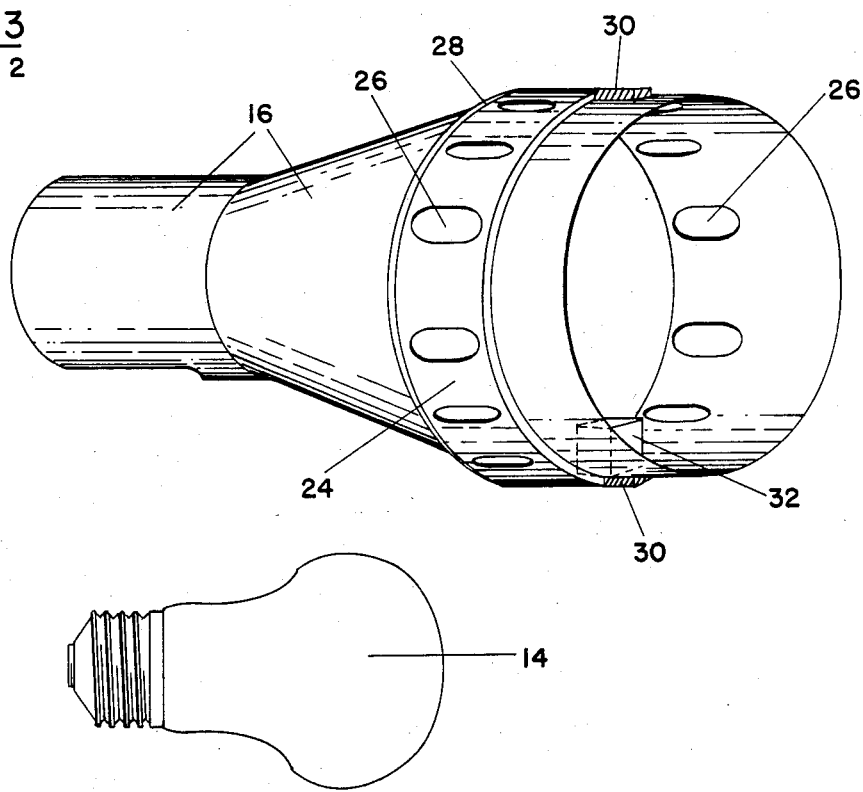
FIG. 3 PART 2

INCANDESCENT LAMP STRUCTURE FOR APPLYING THERAPEUTIC HEAT

BACKGROUND—FIELD OF INVENTION

This invention pertains to incandescent light, especially to a therapeutic incandescent light device that produces a focused and controlled source of light and heat to assist in the prevention and elimination of congestion due to injury, inflammation, or infection of the external, middle, or inner human ear and structures thereof.

BACKGROUND—DESCRIPTION OF PRIOR ART

Because people are continuing to have an ever increasing awareness of personal responsibility in matters pertaining to their wellness, health consumers are continuing to seek methods and devices which they can use to help themselves and their families overcome and prevent health problems.

Heretofore, incandescent light has become such a common place item in our domestic as well our work environment for illumination purposes little thought has been exercised to use it other than for various forms of producing visible light and applications thereof.

Lamps used for therapeutic purposes have appeared in various forms from time to time over the years. Some early forms included arc lamps for general body therapy. These, of course, can not be localized in their use. They produce a high degree of heat that could damage tissue.

In more recent years medical therapeutic lamps have used infrared and/or ultraviolet lights of various forms and sizes. Because of their specialized handling requirements infrared or ultraviolet light is unsatisfactory for deep heat therapy for the ear. The characteristics or burn potential of the infrared and ultraviolet light radiation would preclude their use around the head and neck areas of the body at very close range and in therapeutic amounts.

Of the previous said therapeutic light sources, infrared light has been used for heat therapy on the surface of the body at distances of usually over 18 inches for short periods of time unless used by a trained medical technician. The intensity of heat producing rays from infrared light preclude its use without very close supervision. In fact, infrared heat is such an intense type of heat that it can be used to make a grill that can cook a steak in two minutes.

In 1972, Wideman patented a device referred to as "a perineal heating device." This apparatus does use incandescent light as the light and heat source and the bulb housing has some general appearance which at first glance looks similar. However, the device is used to treat an area of the body quite removed from the ear, namely the post vaginal area of the female body. Its structure with related apparatus prevents it from being used on the ear. It also does not have any way for positive temperature regulation or prevention of over heating.

In 1985, Salia-Munoz patented a device called "a apparatus for applying light through an optical grid." Even though this device does also use incandescent light, it is strictly used for applying various light frequencies to the human skin. It is not used as a heat source at all.

Because problems of the ear due to congestion, inflamation, and infection are such common maladies, especially in children, more and more families are showing a great deal of interest in home therapeutic devices that can assist their family doctor in overcoming the old fashioned "earache" other than the folk remedies that have been handed down from grandma. It is estimated that this device, to be called "Thermo-Ear" TM, will become a mother's best friend when it comes to dealing with painful ears in their children because of its safe, effective, and easy use.

OBJECTS AND ADVANTAGES

Accordingly several objects and advantages of our invention are: to provide a source of controlled and focused deep heat for stimulating circulation within the inner working structure of the human ear so that the pressures caused by injury, inflammation, or infection can be reduced and thereby also reducing the associated pain, to provide the first device that is inexpensive and commercially available on a broad scale for home use to assist in the treatment of earaches, to provide a device that can be used for deep heat therapy that does not require training or supervision to use, to provide a device that the medical practitioners can recommend to assist and comfort their patients at home who have developed pain problems of the ears related to inflammation and/or infection and will synergistically work to potentiate the physician's prescribed regimen.

In addition we claim the following additional objects and advantages: to provide a home therapeutic device that is completely safe from causing over heating or burning of tissue because of the use of a sealed micro thermostat, to provide possible uses in other areas of the body for the management of specific, but localized, inflammatory conditions, and to provide long term reliability and salability because of continued low cost practicality without obsolescence, making it a mother's best friend.

Readers will find further objects and advantages of the invention from a consideration of the ensuing description and the accompanying drawings.

DRAWING FIGURES

FIG. 3 parts 1 and 2 placed side by side and matching connecting projection lines reveals how the parts of the therapeutic device are interrelated in an exploded perspective view.

Figure 2:
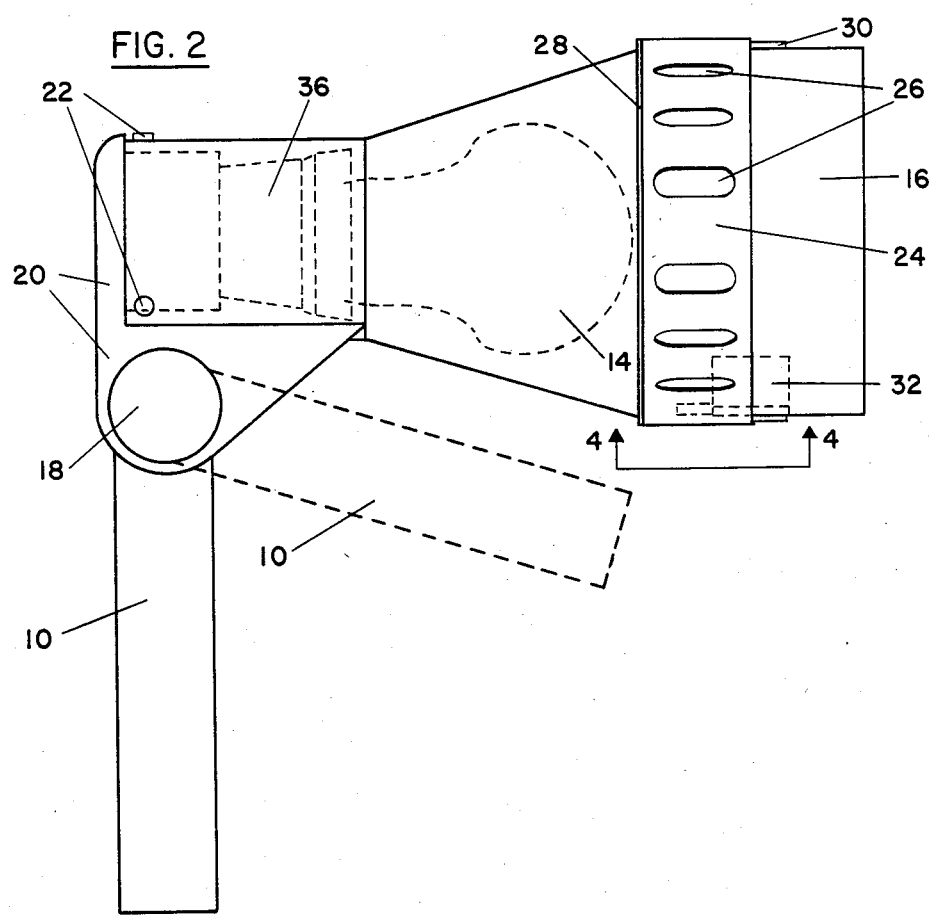
FIG. 2 illustrates a side view of the therapeutic device with some of the lamp housing cutaway to reveal how the inside structure appears.
Figure 4:
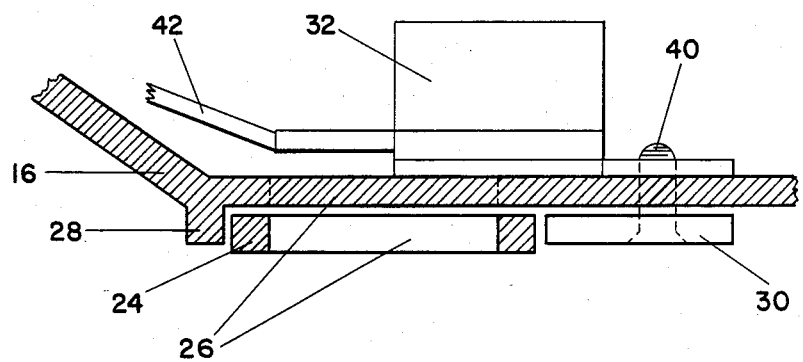

FIG. 4 accompanies FIG. 2 because it is a detail of a cross section of a part of FIG. 2 indicated by the section lines 4—4.

DRAWING REFERENCE NUMERALS:

10: adjustable handle
12: electric cord
14: incandescent appliance light bulb
16: lamp housing
18: handle adjustment knob
20: mounting base
22: 3 screws for retaining lamp housing (16) to mounting base (20)
24: vent ring (adjustable)

26: vent holes
28: rear retaining flange for positioning 24
30: front retaining tabs for maintaining positioning and function of 24
32: thermostat (sealed upper limit type)
34: switch
36: ceramic light bulb socket
38: 2 screws for retaining ceramic bulb socket (36) to mounting base (20)
40: retaining screw for 30 and 32
42: electrical connection for 32
44: pivotal head of 10
46: "O" ring
48: pivotal channel for 52 to pass through
50: paired mounting base holes for 52 and 44
52: threaded part of 18
54: threaded hole of 56
56: lock nut for 18
58: screw holes for housing retention screws 22
60: screw holes for ceramic light bulb socket retention screws 38.

THERAPEUTIC APPLIANCE—DESCRIPTION

Figure 1:
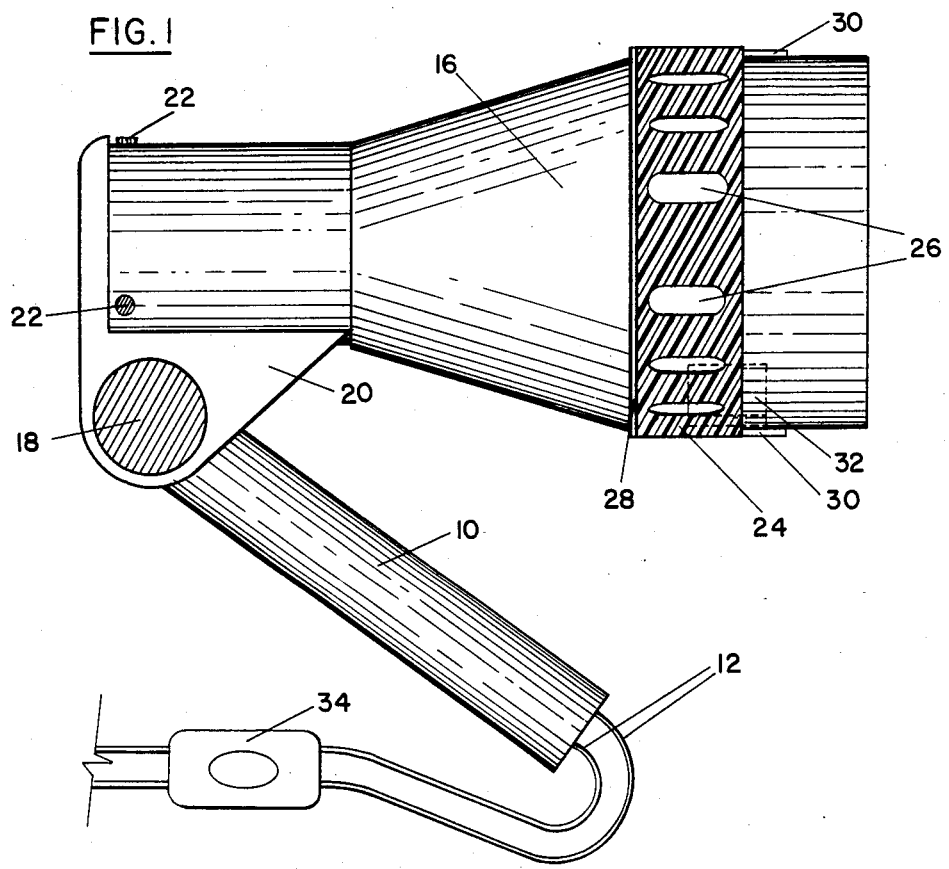
FIG. 1 shows a side view of the therapeutic device as it would look in a functional position when used in therapy of the human ear.

FIG. 1 shows the external appearance of a therapeutic device according to the preferred embodiment of the invention. The external parts of the device are comprised of an adjustable handle 10 through which the electric cord 12 passes to supply current to the incandescent bult 14 (shown in FIG. 2) on the inside of the lamp housing 16. The position of the adjustable handle 10 can be varied by loosening the handle adjustment knob 18 and positioning the adjustable handle 10 to the desired point and retightening handle adjustment knob 18 to hold that new position.

FIG. 1 also shows that the mounting base 20 not only has the adjustable handle 10 attached to it, but also has the lamp housing 16 attached. The lamp housing 16 is held firmly in position by three retention screws 22 of which only 2 are able to be seen in FIG. 1. By looking at FIG. 3 the third lamp housing retention screw 22 can be seen along with its intended position.

It will be noted that the lamp housing 16 has an open end that is shown to be up against the cross sectional diagram of the human ear structure. This end of the therapeutic device contains two important parts. The first is the vent ring 24 (containing twelve vent holes 26) which is held in its position by rear retaining flange 28 and front retaining tabs 30 allowing for rotation of the vent ring 24 when desired. The second important part at the business end of the therapeutic device is shown by phantom lines. This is a thermostat 32 which is manufactured by Fenwal Inc. and is a permanent sealed maximum temperature limiting thermostat. Power is supplied to the whole therapeutic device through the electric cord 12 and is controlled by switch 34.

Going to FIG. 2 will give understanding as to how the therapeutic device looks under the lamp housing 16. When the lamp housing 16 is cut away, it will be noted that the mounting base 20 not only secures the lamp housing 16 in position with the help of three retaining screws 22 (third retaining screw shown in FIG. 3), but also holds a ceramic light bulb socket 36 securely in place by help from two retaining screws 38. The ceramic light bulb socket 36 which is to receive an incandescent appliance light no less than 15 watts and no more than 25 watts.

The details of cross section 4 are shown in FIG. 4 that accompanies FIG. 2. FIG. 4 illustrates how the vent ring 24 relates to the lamp housing 16 and is held in position by rear retaining flange 28 and front retaining tabs 30. FIG. 4 also shows how the thermostat 32 is positioned and secured by retaining screw 40 which also secures one of the front retaining tabs 30. FIG. 4 also shows the electrical connection 42 as it is positioned relative to the location of the thermostat 32 as it is retained within the lamp housing 16.

FIG. 3 has two parts. Part 1 shows the exploded view and interrelations of the adjustable handle 10, the mounting base 20, and the ceramic bulb socket 36. Of particular interest is how the adjustable handle 10 comes together with the mounting base 20. Note also that FIG. 3 reveals how the electric cord 12 negotiates up through the core of adjustable handle 10. The pivotal head 44 of the adjustable handle 10 is designed so that the electric cord 12 can have access to entering the mounting base 20 and allow the handle 10 to be adjusted when necessary without pinching or breaking the electric cord 12.

Part 1 of FIG. 3 also shows how the position of the adjustable handle 10 can be easily changed. The pivotal head 44 of the adjustable handle 10 fits into the base of the mounting base 20 between mounting base holes 50 so that "O" rings 46 will then take their proper relationship between the mounting base 20 and both sides of pivotal head 44. When the pivotal head 44 is positioned correctly in the mounting base 20 the pivot channel 48 of pivotal head 44 will be in line with the paired mounting base holes 50 so that the threaded part 52 of handle adjustment knob 18 can be inserted through the mounting base holes 50 and the pivot channel 48 of pivotal head 44 so that threaded part 52 of handle adjustment knob 18 can engage threaded hole 54 of lock nut 56.

FIG. 3 also shows the location of the three screw retention holes 58 which accept the three screws 22 for retaining lamp housing 16 to mounting base 20. Also the two screw retention holes 60 that accept two retaining screws. 38 for securing ceramic light bulb socket 36 as it sets within the mounting base 20.

Part 2 of FIG. 3 shows the remaining parts of the exploded view in part 1. Lamp housing 16 is shown with the adjustable vent ring 24 and its associated vent holes. Also shown are the rear retaining flange 28 and the front retaining tabs 30 and thermostat 32. Projection lines show how the lamp housing 16 and associated parts relate to the mounting base 20 and its parts. Incandescent appliance light bult 14 is shown in its projection to the ceramic lamp socket 36.

THERAPEUTIC DEVICE—OPERATION

The therapeutic device as shown in various ways from FIGS. 1 through 4 will provide a source of controlled and focused deep heat for the relief of pain in the human ear due to infection, inflammation, or injury. Deep heat provides a circulatory stimulation due to blood vessel dilation. When the blood vessels dilate the congestion and pressure from various inflammations and infections that produce pain are relieved.

In order to use the device it has to be plugged in to an electrical outlet and have a 15 to 25 watt incandescent appliance light bulb 14 screwed into the ceramic light bulb socket 36. Before the switch 34 is turned to the on position, the adjustable handle needs to be set at the most comfortable point for the user to hold while giving therapy. Some users may feel more comfortable loosening the handle adjustment knob 18 and placing the adjustable handle 10 in a fully extended vertical position as shown in FIG. 3. While others may want to place the adjustable handle in the partially extended position as shown in FIG. 1. Whatever position is desired, the handle adjustment knob 18 must first be loosened (counter clockwise) before adjustable handle 10 can be moved. Once the handle 10 is placed in the desired position, the handle adjustment knob 18 can be tightened in the usual clockwise direction to maintain the newly established position.

When the switch 34 is placed in the on position the incandescent bulb begins to glow producing light and heat. As shown in FIG. 1, the device is in treatment position when it is placed against the ear while the incandescent appliance light bulb 14 is illuminated. The device can be used in this position for as long as a physician might recommend or until relief from pain and or drainage is established.

During use the therapeutic device will continue to produce heat. The maximum potential temperature that the device could reach is dependent on the size of the appliance bulb being used. However, the continuous functioning sealed upper limit thermostat 32 protects against temperatures increasing to points where burning and injury to the user may result.

The adjustable vent ring 24, which is shown in FIGS. 1 through 4 and contains the 12 vent holes, is also used to control heat build up. Many times the user may not want as warm of temperatures as the upper limit thermostat allows. This means that the adjustable vent ring 24 which is held in its specific working bounds by the rear retaining flange 28 and front retaining tabs 30 can be turned so that the vent holes 26 in both the vent ring 24 and the lamp housing 16 will line up to allow warm air to escape the inside of the lamp housing thus lowering the temperature. The extent to which the vent holes 26 line up will determine how much heat is allowed to escape through them. Therefore, a user can deliver any amount of heat to the ear up to the temperature limit of the safety thermostat.

This therapeutic device is designed to be completely safe and simple to use by adults and older children. It can work well with small children and infants when it is used by the parent for ear therapy.

Thus the reader will see that the this therapeutic device provides a simple, highly effective, accurate, reliable, safe, and economical way of providing deep heat treatment for various and frequently encountered ear problems. However, while the description contains several specificities, these should not be construed as limitations on the scope of the invention, but rather as an exemplification of one preferred embodiment thereof. Many other variations of use are possible. For example, it is foreseen that with the capability for the application of focused heat without undue pressure this therapeutic device could be used to treat other parts of the body for the management of specific, but localized, inflammatory conditions. One such application would be for the heat treatment of some forms of hemorrhoid inflammations. Another would be where heat is needed to bring about heading of a boil in a particular location on the surface of the body. Again this device could be adapted for similar use in various veterinary therapies. Accordingly the reader is requested to determine the scope of the invention by the appended claims and their legal equivalents, and not by the examples which have been given.

We claim:

1. A controlled incandescent heat lamp for therapy of the live human ear structure to help treatment of pain and congestion due to injury, inflammation, or infection comprising:

a mounting base with an adjustable handle having an attached ceramic light bulb socket covered by a lamp housing open at one end, said opening in said lamp housing constituting means for directing light and heat at a human ear using approximately a 15 to 25 watt incandescent appliance light inserted in said ceramic light bulb socket, a sealed upper limit thermostat attached just inside said opening of said lamp housing means of preventing excessive heat and potental burning and injury while in use, means for additional temperature adjustment through a vent ring on the outside of said lamp housing, said vent ring constituting means for adjustable rotation to align and disalign vents of said ring and said lamp housing so a desired amount of heat is released during use, whereby a simple, accurate, safe, and economical way of adding a new dimension for using light and heat in assisting the treatment of earaches and infections plus other applications where heat without undue pressure can be used to manage specific, but localized, inflammatory conditions.

2. Apparatus for applying light and heat energy to the live human ear structure including in combination an incandescent light source of approximately 15 to 25 watts, a mounting base to which said light source is attached, an adjustable handle attached to said mounting base, a lamp housing also attached to said mounting base constituting means for directing light and heat of said incandescent light through open end, an opening in said lamp housing constituting means for placing the lamp over an ear, further comprising a vent ring as a part of said lamp housing constituting means for adjusting to align and disalign vent holes of said vent ring and said lamp housing for releasing a desired amount of heat and for lowering the temperature of heat to the ear at greater amounts than a sealed upper limit thermostat automatically allows, said sealed upper limit thermostat attached inside of said open end of said lamp housing means of safely preventing overheating and tissue damage during use, whereby light and heat therapy can be given to relieve pain causing congestion that may have resulted from injury, inflammation, or infection that may have effected various of the ear structures, and whereby there is provided means for applying heat without undue pressure where needed to manage specific, but localized, inflammatory conditions, plus being simple, accurate, safe, and economical in all aspects of use.

* * * * *